United States Patent [19]

Tansley

[11] Patent Number: 5,221,529

[45] Date of Patent: Jun. 22, 1993

[54] COSMETIC COMPOSITION

[75] Inventor: Sally E. Tansley, Frankby, England

[73] Assignee: Chesebrough-Pond's USA Co., Division of Conopco, Inc., Greenwich, Conn.

[21] Appl. No.: 667,982

[22] Filed: Mar. 12, 1991

[30] Foreign Application Priority Data

Mar. 12, 1990 [GB] United Kingdom ............... 9005522

[51] Int. Cl.$^5$ ..................... A61K 7/32; A61K 7/42; A61K 7/44; A61K 7/48

[52] U.S. Cl. ........................ 424/65; 424/DIG. 5; 424/59; 424/60; 424/66; 424/67; 424/68; 514/844

[58] Field of Search .............. 424/65, DIG. 5, 67, 424/66, 68

[56] References Cited

U.S. PATENT DOCUMENTS

| | | | |
|---|---|---|---|
| 4,322,400 | 3/1982 | Yuhas | 424/67 |
| 4,493,786 | 1/1985 | Joshi | 252/368 |
| 4,504,465 | 3/1985 | Sampson et al. | 424/68 |
| 4,524,062 | 6/1985 | Laba et al. | 424/65 |
| 4,584,126 | 4/1986 | Joshi | 252/362 |
| 4,617,185 | 10/1986 | DiPietro | 424/68 |
| 4,650,670 | 3/1987 | Callingham et al. | 424/65 |
| 4,741,899 | 3/1988 | Henry et al. | 424/47 |
| 4,759,924 | 7/1988 | Luebbe et al. | 424/68 |

FOREIGN PATENT DOCUMENTS

| | | | |
|---|---|---|---|
| 0120210 | 10/1984 | European Pat. Off. | 424/65 |
| 0089120 | 7/1987 | European Pat. Off. | 424/65 |
| 1178599 | 8/1986 | Japan | 252/106 |
| 61-190598 | 7/1989 | Japan | 252/106 |

*Primary Examiner*—Dale R. Ore
*Attorney, Agent, or Firm*—Milton L. Honig

[57] ABSTRACT

A transparent cosmetic composition in stick form comprising:
(a) from 20 to 70% by weight of glycerol
(b) from 3 to 20% by weight of a fatty acid soap
(c) from 0 to 20% by weight of water
(d) from 15 to 65% by weight of an alcohol other than glycerol.

4 Claims, No Drawings

COSMETIC COMPOSITION

FIELD OF INVENTION

The invention relates to cosmetic transparent stick formulations. More particularly, it relates to deodorant stick compositions with a high level of transparency and good stability, containing as essential ingredients a long-chain fatty acid soap, glycerol and an alcohol other than glycerol.

BACKGROUND AND PRIOR ART

Cosmetic sticks are well known as delivery systems for deodorants, antiperspirants, astringents and medicaments. Sticks are advantageous over aerosols in that they obviate the need for a fluorocarbon propellant which may cause environmental damage.

Conventionally, transparent cosmetic compositions have been made using a soap/alcohol formulation. Such compositions have been formed as gel sticks which act as vehicles for delivery of active ingredients, such as perfumes and bactericides. Propylene glycol or ethanol are commonly used as solvents.

Sticks based on soap (e.g. sodium stearate), propylene glycol and ethanol are desirable in producing a pleasant cooling effect on the skin but it is found that to obtain moderate degrees of cooling, transparency is lost. This is exemplified in patent EP 107 330 (Procter & Gamble) which describes a deodorant gel stick containing hydroalcoholic soluble emollients. The composition contains less than 12.5% of a short-chain monohydric alcohol, e.g. ethanol.

U.S. Pat. No. 4,268,498 (Revlon) describes clear cosmetic sticks comprising a soap/alcohol gel base. It proposes the use of polyoxyethylene-glucose fatty acid esters and of ethers of long-chain alcohols to replace short-chain monohydric alcohols. In this case the term "clear stick" is not strictly accurate and refers to a translucent as well as transparent stick.

We have now found that the problems of combining transparency with a level of alcohol which will give a stable transparent soap-based stick with desirable cooling effect may be overcome by using glycerol as the humectant/solvent. This results in a stable, transparent stick. Other solvents may also be present, such as propylene glycol and water. Varying the content of these other solvents may optimise the sensory feel of the product.

DEFINITION OF THE INVENTION

The invention provides a transparent cosmetic composition comprising:
(a) from 20 to 70% by weight of glycerol;
(b) from 3 to 20% by weight of a soap;
(c) from 0 to 20% by weight of water;
(d) from 15 to 65% by weight of an alcohol other than glycerol.

DISCLOSURE OF THE INVENTION

Glycerol, when used to replace at least part of the propylene glycol in standard soap gelled stick formulations, causes a fundamental change in the stick structure. Surprisingly, and unlike other polyols, with glycerol the sticks are transparent and birefringent domains can be seen.

The present invention further relates to transparent gel sticks with a wide range of sensory feel.

(A) The Structure

Thin slices (approximately 5 mm) of the sticks according to the present invention when taken and viewed through cross-polarising lenses show distinct birefringent domains indicative of a unique structure. The size of these domains is determined by the solvents utilized and the processing procedures. The number of domains apparently determines the degree of transparency; a large number of very small domains or a few large domains leads to a transparent stick. Domain sizes and numbers between these extremes are not as transparent.

(B) Transparency

Transparency was evaluated in two ways:
(a) the test given in U.S. Pat. No. 3,274,119 wherein "transparent: is defined as such that a bold face of 14 point size can be readily read though a $\frac{1}{4}$" section of material;
(b) transparency as measured objectively by a consumer panel of a minimum of 15 panellists.

(C) Composition

By careful manipulation of solvent ratios the sensory properties of the transparent sticks can be varied and the transparency of the stick retained.

(i) The Solvent

The solvent comprises from 20 to 70% by weight of the trihydric alcohol glycerol. Transparency has been found to depend on the level of glycerol present, the higher the percentage of glycerol, the greater the degree of transparency. The solvent additionally comprises alcohols other than glycerol. Such other alcohols include simple short chain alcohols such as ethanol, and are within the range 15 to 75%, preferably 15-50%. The ratio of such alcohols to glycerol may range from 1:4 to 4:1, preferably from 1:3 to 2:1.

The sensory feel of a stick can be manipulated if the alcohol other than glycerol comprises an additional polyol such as propylene glycol. To maximise the transparency the ratio of glycerol to the alcohol other than glycerol should preferably remain above about 1:1, it being generally observed that the stick has a higher degree of transparency the higher the level of glycerol that it contains. However, it has been observed that formulations containing above about 75% glycerol can be undesirably sticky.

(ii) The soap

The composition according to the invention comprises a soap. Preferably the soap is a straight chain saturated soap with chain length of at least $C_{16}$, and especially it may comprise a mixture of palmitate and stearate. The soap is present in an amount from 3 to 20% by weight. The soap may be neutralised with alkali metal, alkaline earth, alkanol ammonium or any other suitable cation.

(iii) Water

The composition according to the invention comprises from 0 to 20% by weight of water.

(iv) Other ingredients

In addition to the essential ingredients defined herein, there may also be included in the cosmetic composition of the invention other ingredients, provided they do not destroy the transparency of the composition. Examples of additives are emollients, perfumes, dyes, anti-microbial agents, deodorants, deo-perfumes, sunscreens, skin modifiers and coolants (e.g. menthol) as well as other additives known in this field.

ADVANTAGES OF THE INVENTION

The transparent cosmetic composition of the invention may be formed as a solid transparent stick. By selection of suitable packaging, it is possible to avoid the problem of shrinkage due to evaporation of alcohol. The composition of the invention retains its transparency on storage.

PROCESS OF MANUFACTURE

The invention also provides a process for preparing a transparent cosmetic composition as herein defined. The process comprises combining the ingredients in liquid form. To manufacture a transparent stick, the combined ingredients are poured into a container having a particular shape so that the solid which forms takes the shape of the container.

If sticks containing very low levels of water are to be made, sodium hydroxide may be added to the alcohol and the solution heated with constant stirring to reflux. When completely dissolved all the remaining ingredients except the perfume, anti-bacterial agent and the like minor ingredients may be added, the solution stirred and once more heated to reflux. Finally, the solution is cooled to about 60° C., minor ingredients such as perfume added to the homogenous solution and the sticks cast into appropriate barrels.

PRODUCT FORMS AND PACKAGING

A preferred embodiment of the invention is in the form of a stick of circular or oval cross-section contained in a stick dispenser. Suitable dispensers have an airtight cap so as to prevent evaporation of volatile ingredients during storage between uses. The composition of the invention can also be dispensed as a cream or soft gel from an applicator suitable for the purpose.

USE OF THE INVENTION

The transparent cosmetic composition of the invention is applied to areas of the skin as desired. In the case of a transparent stick, the stick is rubbed on the skin so as to leave a deposit of the cosmetic composition. By this means, additives which are included in the cosmetic composition may be spread onto the skin in the quantities required. The stick may also be used for application of medicament.

EXAMPLES

Examples of cosmetic sticks were prepared according to Table I (examples 1-9). Also prepared were comparative examples A-D, without glycerol.

Table II compares transparency, smoothness and coolness of the examples of table I, including comparative examples A-D (scored by a panel, averaged out of 100).

TABLE I

| Example | IMS (Alcohol) | Glycerol | $C_{16}C_{18}$ Fatty Acid | NaOH | Water | Propylene Glycol | Perfume | Miscellaneous (Deo-active for colour) |
|---|---|---|---|---|---|---|---|---|
| 1 | 25.1 | 67.0 | 6.0 | 0.9 | — | — | 1.0 | — |
| 2 | 25.1 | 66.9 | 6.0 | 0.9 | — | — | 1.0 | 0.1 |
| 3 | 25.0 | 29.05 | 6.4 | 1.0 | 7.5 | 29.05 | 1.0 | 1.0 |
| 4 | 35.0 | 51.6 | 6.4 | 1.0 | 5.0 | — | 1.0 | — |
| 5 | 46.65 | 45.45 | 6.0 | 0.9 | — | — | 1.0 | — |
| 6 | 28.01 | 50.0 | 6.0 | 0.9 | 14.0 | — | 1.0 | — |
| 7 | 37.3 | 36.2 | 6.0 | 0.9 | 18.6 | — | 1.0 | — |
| 8 | 46.0 | 44.9 | 7.0 | 1.1 | — | — | 1.0 | — |
| 9 | 46.0 | 44.8 | 7.0 | 1.1 | — | — | 1.0 | 0.1 |
| A | 65.0 | — | 6.4 | 1.0 | — | 26.6 | 1.0 | — |
| B | 37.2 | — | 6.0 | 0.9 | 18.7 | 36.2 | 1.0 | — |
| C | 46.0 | — | 7.0 | 1.1 | — | 44.9 | 1.0 | — |
| D | 35.0 | — | 6.4 | 1.0 | 1.0 | 5.0 | 1.0 | — |

(All figures are parts by weight of the composition)

TABLE II

| EXAMPLE | 1 | 2 | 3 | 4 | 5 | 6 | 7 | 8 | 9 | A | B | C | D |
|---|---|---|---|---|---|---|---|---|---|---|---|---|---|
| Transparency of stick | 84 | 80 | 33 | 61 | 54 | 53 | 43 | 69 | 68 | 20 | 17 | 28 | 29 |
| Coolness of skin | 37 | 33 | 35 | 42 | 43 | 36 | 59 | 37 | 52 | 48 | 60 | 45 | 47 |
| Smoothness of stick | 42 | 26 | 62 | 41 | 75 | 70 | 84 | 46 | 62 | 84 | 88 | 74 | 77 |

I claim:

1. A transparent cosmetic composition in stick form comprising:
   (a) from 20 to 70% by weight of glycerol;
   (b) from 3 to 20% by weight of a fatty acid soap;
   (c) from 0 to 20% by weight of water; and
   (d) from 15 to 65% by weight of an alcohol other than glycerol, and wherein the ratio of glycerol to the alcohol is greater than about 1:1.

2. A transparent cosmetic composition according to claim 1 wherein the soap comprises a mixture of palmitate and stearate.

3. A transparent cosmetic composition according to claim 1, wherein the ratio of glycerol to the alcohol other than glycerol is greater than about 1:1.

4. A transparent cosmetic composition according to claim 1 wherein thin slices of approximately 5 mn of the stick when taken and viewed through cross-polarizing lenses shows distinct birefringement domains.

* * * * *